United States Patent [19]

Kanesaka

[11] Patent Number: 5,330,499
[45] Date of Patent: Jul. 19, 1994

[54] CATHETER EXCHANGE SYSTEM

[76] Inventor: Nozomu Kanesaka, 36 Cathy Rd., Hillsdale, N.J. 07642

[21] Appl. No.: 998,089

[22] Filed: Dec. 28, 1992

[51] Int. Cl.⁵ .......................... A61M 29/00
[52] U.S. Cl. ..................... 606/194; 606/191; 604/96
[58] Field of Search .............. 604/93, 95, 96; 606/191, 194

[56] References Cited

U.S. PATENT DOCUMENTS

| | | | |
|---|---|---|---|
| 4,762,129 | 8/1988 | Bonzel | 606/194 |
| 4,892,519 | 1/1990 | Songer et al. | 606/194 |
| 4,943,278 | 7/1990 | Euteneuer et al. | 606/194 |
| 4,944,745 | 7/1990 | Sogard et al. | 606/194 |
| 5,046,503 | 9/1991 | Schneiderman | 606/194 |
| 5,135,535 | 8/1992 | Krama | 606/194 |
| 5,180,367 | 1/1993 | Kontos et al. | 606/194 |
| 5,195,971 | 3/1993 | Sirhan | 604/96 |

*Primary Examiner*—C. Fred Rosenbaum
*Assistant Examiner*—N. Kent Gring
*Attorney, Agent, or Firm*—Kanesaka & Takeuchi

[57] ABSTRACT

A dilation catheter of the invention is formed of a flexible tube having distal and proximal ends, and a balloon attached to the distal end of the tube. The catheter includes a first opening formed in the tube to communicate with the balloon, and a second opening formed in the tube near the proximal end of the balloon. A partition is located inside the tube to communicate the proximal end of the tube with the first opening. Thus, inflation and deflation of the balloon attached to the tube can be controlled by fluid applied through the tube. A guide wire extends through the tube between the distal end and the second opening.

7 Claims, 2 Drawing Sheets

CATHETER EXCHANGE SYSTEM

BACKGROUND OF THE INVENTION AND RELATED ART STATEMENT

The present invention relates to angioplasty apparatus for providing a dilation catheter to facilitate a quick exchange of the dilation catheter.

The dilation catheter is introduced into a body of a patient to enlarge constrictions in blood vessels and other body cavities. In one of conventional dilation catheters, an inner lumen is situated inside an outer lumen, and a balloon is attached to the distal end of the outer lumen. A guide wire is located inside the inner lumen.

In this method, firstly, a guide wire is introduced into a desired location, and secondly, the inner lumen with the outer lumen over the guide wire is pushed over the introduced guide wire to the desired location. The inner and outer lumens may be introduced into a blood vessel together with the guide wire.

However, should the need to exchange the introduced catheter, for example to change the size of the balloon, the guide wire must be protruded from the patient's body by a length greater than the length of the dilation catheter. Therefore, an extension wire is attached to the first introduced guide wire. When the catheter is changed, the guide wire is held firm in location, the dilation catheter in the blood vessel is withdrawn, and the new dilation catheter is introduced over the guide wire to complete the exchange. The handling of the extended guide wire is very cumbersome because of the length of the guide wire.

In order to solve the above problem, a short inner lumen is attached to a long outer lumen to extend from the distal end of the outer lumen. The proximal end of the inner lumen is sealingly attached to a side wall of the outer lumen near the distal end thereof. An inflatable balloon is attached between the distal ends of the inner and outer lumens. The guide wire passes through the inner lumen to advance or retract the catheter on the guide wire. The outer lumen has a port on the proximal end, and the balloon is capable of being inflated or deflated through the outer lumen from the proximal end by means of a syringe or other devices.

In the above improved catheter, since the guide wire passes only through the short inner lumen, the catheter can be exchanged easily without using the extension guide wire.

In U.S. Pat. No. 4,762,129, a short tube for guiding the guide wire is attached to the distal end of a long tube. A balloon is also attached to the distal end of the long tube, and a fluid is introduced into the balloon through the long tube.

Although these improved systems mentioned above may avoid the requirements for using the long extended guide wires, the coaxial and dual lumens are attached to the proximal end of the balloon, so that the outer diameter becomes larger as well as the distal end of the catheter is too stiff to follow the bending vessels. Further, in the dual lumen design where the short tube is attached to the long tube, the rotation and pushability of the dilation catheter are reduced since the inner lumen tracking on the guide wire is pushed with the outer lumen in the offset position.

The same can be said on the coaxial design, since the outer lumen does not extend to the distal end of the balloon. Namely, the only common junction between the outer and inner lumens is the one where the proximal end of the inner lumen is exiting from the outer lumen.

In the angioplastisy, the above lumens are generally guided by a guide catheter, and as the blood vessel becomes a small diameter, the lumens are extended from the guide catheter. Thus, the design of the two lumen catheters with the guide wire exiting from the guide catheter increases the outer diameter of the guide catheter or the total size of the dilation catheter to thereby limit the ability of the introduction of two or more of the dilation catheters in the same guide catheter of a small size.

Accordingly, an object of the invention is to provide a dilation catheter to obviate the foregoing difficulties.

Another object of the invention is to provide a dilation catheter as stated above, which has a small diameter and can be controlled easily without trouble.

A further object of the invention is to provide a dilation catheter as stated above, which can be easily manufactured.

Further objects and advantages of the invention will be apparent from the following description of the invention.

SUMMARY OF THE INVENTION

In accordance with the present invention, a dilation catheter is formed of a flexible tube, and a balloon attached to the distal end of the tube. A first opening is formed in the tube to communicate with the balloon, and a second opening is formed in the tube near the proximal end of the balloon.

A partition is located inside the tube to communicate the proximal end of the tube with the first opening. Thus, the inflation and deflation of the balloon attached to the tube can be controlled by fluid applied through the tube. A guide wire for leading the catheter passes through the tube between the distal end and the second opening.

In the invention, the tube constitutes a single lumen to facilitate quick exchange capability as! well as to provide a better axial force and torque transmission. The use of the partition with the single lumen minimizes the over all size or thickness, resulting in a better flexibility and transition of force applied to the lumen. As a result, the catheter can be lead smoothly to tight lesions.

DETAILED DESCRIPTION OF PREFERRED EMBODIMENTS

Figure 1:
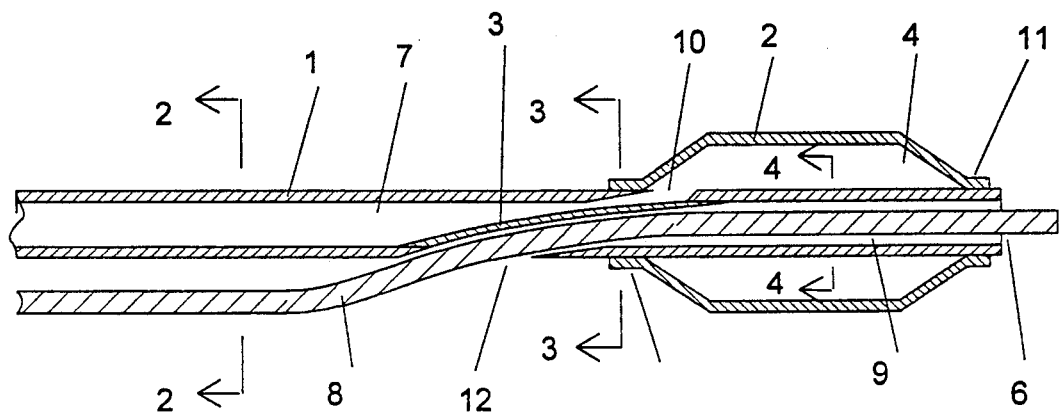
FIG. 1 shows a section view of a main part of a first embodiment of a dilation catheter with a guide wire according to the invention.
Figure 2:
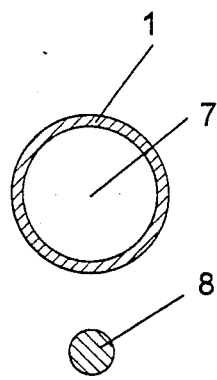
FIG. 2 shows a cross section view taken along a line 2—2 in FIG. 1 of the dilation catheter with the guide wire.
Figure 3:
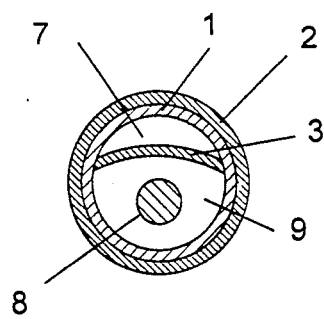
FIG. 3 shows a cross section view taken along a line 3—3 in FIG. 1 of the dilation catheter with the guide wire.
Figure 4:
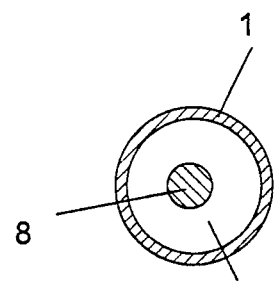
FIG. 4 shows a cross section view taken along a line 4—4 in FIG. 1 of the dilation catheter in the region of the balloon.

In the typical angioplasty treatment, a guide catheter, not shown in the drawing, having a diameter of several millimeters and a length of about one meter, is introduced from a patient's right groin throughout the length of the artery to the aorta. A guide wire 8 in FIG. 1, which is slightly longer than the guide catheter, is introduced through the guide catheter and advanced to pass the lesion in the patient's vessel. The guide wire 8 is used to track or guide the dilatation catheter.

The dilation catheter is formed of a single lumen 1, a balloon 2 attached to the lumen 1, and a partition 3 situated inside the lumen 1, as shown in FIG. 1. The lumen 1 further includes openings 10, 12. The partition 3 sealingly divides the inside of the lumen 1 into first and second channels 7, 9.

The first channel 7 communicates with an interior 4 of the balloon 2 through the opening 10, while the second channel 9 communicates with the opening 12. The first channel 7 is used to inflate and deflate the balloon 2, and the second channel 9 is used to track the guide wire 8. The channel 7 is completely sealed from the channel 9 by the partition 3.

The balloon 2 is formed of an outer envelope and is sealed to the lumen 1 at a distal end 11 and a proximal end 5 to complete the sealed enclosure. The balloon 2 is inflated and deflated through the opening 10 when fluid is introduced or withdrawn through the first channel 7 from a port at the proximal end of the lumen 1.

In use, the dilation catheter is assembled with the guide wire 8 such that the guide wire 8 passes through the second channel 9 from the opening 6 and exits at the opening 12. The catheter may be advanced in the vessel of the patient by securing the position of the guide wire 8 relative to the guide catheter. When the distal end of the lumen 1 is arrived at the desired location, fluid is supplied to inflate the balloon 2 for the dilation of the lesion. Thereafter, when the catheter is withdrawn, the fluid inside the balloon 2 is discharged through the lumen 1. Then, the guide wire 8 is held and the single lumen catheter is removed along the guide wire 8.

When the dilation catheter is exchanged while using, e.g. for changing the size of the balloon, the guide wire 8 is held in position, and the dilation catheter is taken out of the blood vessel along the guide wire 8. Then, a different dilation catheter is placed over the guide wire 8, and is advanced along the guide wire 8.

In the invention, since the channel 9 in the lumen 1 is short, the dilation catheter can be easily exchanged without using a long guide wire. Also, since the size or thickness of the lumen 1 is small, the dilation catheter can be advanced to a small blood vessel.

Figure 5:
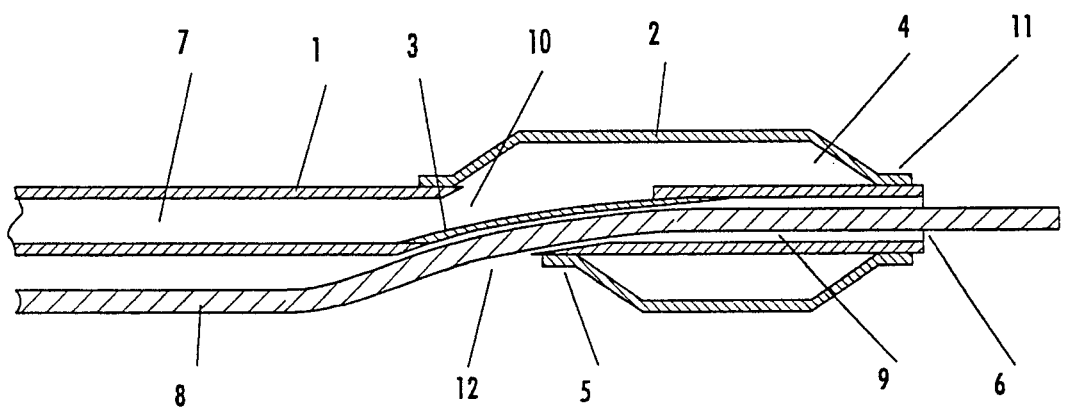
FIG. 5 shows a side view of a second embodiment of the dilation catheter of the invention.

FIG. 5 shows an alternative embodiment of the dilation catheter of the invention, wherein the proximal end of the balloon 2 is attached to the lumen 1 in an offset condition. Thus, it is possible to form a large hole 10 to thereby easily and quickly inflate and deflate the balloon.

While the invention has been explained with reference to the specific embodiments of the invention, the explanation is illustrative and the invention is limited only by the appended claims.

What is claimed is:

1. A dilation catheter comprising,
   one flexible tube having an outer surface, an elongated hole extending throughout an entire length of the tube, and distal and proximal ends,
   a balloon attached to the outer surface of the tube near the distal end thereof and having distal and proximal ends,
   a first opening formed in the tube to communicate the hole with the balloon,
   a second opening formed in the tube near the first opening to communicate the hole with an outside of the tube, and
   a partition in a form of a single separating wall located inside the tube to sealingly divide the elongated hole into first and second hole portions, said partition extending form a portion near proximal of the second opening to a portion near distal of the first opening, said first hole portion communicating with the proximal end of the tube and the first opening so that inflation and deflation of the balloon attached to the tube can be controlled by fluid applied through the first hole portion, said second hole portion communicating with the distal end and the second opening to allow a guide wire to pass therethrough.

2. A dilation catheter according to claim 1, wherein said partition is disposed diagonally inside the hole to allow the guide wire to smoothly pass through the second hole portion in he tube.

3. A dilation catheter according to claim 1, wherein said second opening is located away form the first opening, said first opening being located close to the distal end of the tube.

4. A dilation catheter according to claim 1, wherein said first and second openings are located at same distances away from the distal end of the tube.

5. A dilation catheter according to claim 4, wherein the balloon has an offset portion, said second opening being formed at the offset portion to thereby facilitate communication between the balloon and the proximal end of the tube.

6. A dilation catheter according to claim 1, wherein said partition is secured immediately proximal of the second opening and immediately distal of the first opening and extends inside the tube therebetween to divide the tube into two.

7. A dilation catheter according to claim 6, wherein said distal end of the balloon is fixed to the outer surface of the tube at the distal end thereof, and the proximal end of the balloon is fixed to the outer surface of the tube away form the distal end of the tube.

* * * * *